(12) United States Patent
Anhalt

(10) Patent No.: US 8,999,428 B2
(45) Date of Patent: Apr. 7, 2015

(54) ORTHOPEDIC CUSHION AND METHOD FOR PRODUCTION THEREOF

(75) Inventor: Klaus-Peter Anhalt, Rhumspringe (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 279 days.

(21) Appl. No.: 13/140,512

(22) PCT Filed: Dec. 16, 2009

(86) PCT No.: PCT/EP2009/009012
§ 371 (c)(1),
(2), (4) Date: Sep. 13, 2011

(87) PCT Pub. No.: WO2010/078924
PCT Pub. Date: Jul. 15, 2010

(65) Prior Publication Data
US 2011/0320011 A1  Dec. 29, 2011

(30) Foreign Application Priority Data

Dec. 19, 2008  (DE) .......................... 10 2008 063 818

(51) Int. Cl.
A61F 2/80 (2006.01)
B05D 3/02 (2006.01)
B05D 3/00 (2006.01)
A61F 5/34 (2006.01)
A61F 2/50 (2006.01)
A61F 2/78 (2006.01)
A61L 15/12 (2006.01)
A61L 15/14 (2006.01)
C08G 61/02 (2006.01)

(52) U.S. Cl.
CPC .................. A61F 5/34 (2013.01); A61F 2/5044 (2013.01); A61F 2/7812 (2013.01); A61L 15/12 (2013.01); A61L 15/14 (2013.01); C08G 61/02 (2013.01); A61F 2002/501 (2013.01); A61F 2002/5086 (2013.01); C08G 2261/3424 (2013.01)

(58) Field of Classification Search
USPC ..................................... 427/2.26, 322; 623/36
See application file for complete search history.

(56) References Cited

U.S. PATENT DOCUMENTS

| | | | |
|---|---|---|---|
| 3,246,627 A | 4/1966 | Loeb et al. | |
| 3,301,707 A | 1/1967 | Loeb et al. | |
| 3,600,216 A | 8/1971 | Stewart | |
| 5,484,560 A * | 1/1996 | Moriyama et al. | 264/483 |
| 5,603,122 A | 2/1997 | Kania | |
| 5,830,237 A | 11/1998 | Kania | |
| 6,051,169 A * | 4/2000 | Brown et al. | 264/40.1 |
| 6,071,987 A * | 6/2000 | Matsumoto et al. | 523/209 |
| 6,270,872 B1 | 8/2001 | Cline et al. | |
| 6,634,369 B2 * | 10/2003 | Jared et al. | 134/22.1 |
| 6,790,318 B2 * | 9/2004 | Lai et al. | 202/169 |
| 6,964,688 B1 | 11/2005 | Kania | |
| 7,291,182 B1 | 11/2007 | Kania | |
| 8,523,951 B2 | 9/2013 | Kania | |
| 2002/0182392 A1* | 12/2002 | Welch et al. | 428/216 |
| 2004/0068048 A1* | 4/2004 | Giles et al. | 524/588 |
| 2006/0111792 A1* | 5/2006 | Shannon | 623/36 |

FOREIGN PATENT DOCUMENTS

| | | |
|---|---|---|
| CN | 1427701 A | 7/2003 |
| CN | 201160923 Y | 12/2008 |
| DE | 20315575 U1 | 1/2004 |
| DE | 20315575 U1 * | 2/2004 |
| WO | 03051241 A1 | 6/2003 |
| WO | WO 03051241 A1 * | 6/2003 |

OTHER PUBLICATIONS

Machine Translation DE20315575 U1 Feb. 2004.*
PCT International Search Report for Application No. PCT/EP2009/009012, mailed Oct. 29, 2010.
Chinese Search Report for Application No. 200980151143.X, mailed Aug. 21, 2013 (2 pp.).

* cited by examiner

Primary Examiner — Cachet Sellman
(74) Attorney, Agent, or Firm — Holland & Hart

(57) ABSTRACT

The invention relates to an orthopedic cushion made from a filled elastomer or softened thermoplastics and can be provided with a thin friction-reducing coating made from a non-polar, non-hydrophilic slip-increasing polymer coating namely poly(para-xylene). According to the invention, the above can be achieved by means of a method in which the polymerized polyurethane cushion is subjected to at least one pretreatment step in which volatile components are removed to such an extent as to be able to be immediately coated.

16 Claims, No Drawings

ORTHOPEDIC CUSHION AND METHOD FOR PRODUCTION THEREOF

TECHNICAL FIELD

The invention relates to a process for producing an orthopedic cushion which has a friction-reducing coating and which is made of a filled elastomer, of an elastomer gel, of a plasticized thermoplastic, or of a polyurethane, to a novel orthopedic cushion thus obtainable, and to the use of the coating material poly(para-xylylene) on an orthopedic cushion.

BACKGROUND

Orthopedic cushions are used inter alia for cushioning between orthopedic aids and parts of the body, for example for cushioning between prosthetic parts, orthosis parts, or frame parts and the body of the user. Among the orthopedic cushions here are in particular those known as liners and sockets.

An orthopedic liner is a cover which has a cushioning or shaping function, for the distal end of the stump of a limb, or of a limb. The term liner is generally also understood to mean any material which has a cushioning and shaping function and takes the form of a stocking, of a cover, of a band, or of a patch, intended to cushion the boundary between a body part and an orthopedic means, e.g. a prosthetic socket, a support device, or an orthotic.

In particular the stump liners must fit well, like stump stockings, and for application they are therefore turned inside out and rolled onto the stump. This exposes the liner material to severe mechanical stress, and it has to be flexible and highly elastic. The liners are exposed to high tensile forces when they are pulled onto the stump. For the patient, the procedure can be very arduous and difficult. Application aids and application sprays are therefore available, but the latter can be hazardous to health.

In order to reduce friction levels on the external side of the liner, some known liners provide (friction-reducing) coatings which increase slip capability. However, the mode of action of a coating that provides slip is often based on smoothing at the surface, and the layer thicknesses in which the known coatings have to be applied are relatively high. The coating can then impair those properties of the liner material that are desired for its functioning. This also applies in principle to other types of cushion.

WO 03/051241 A1 discloses an elastomer liner coated with poly(para-xylylene). Said coating is applied by chemical vapor-phase deposition (CVD) and features excellent slip capability. It bonds well to silicone and to unfilled synthetic rubbers. The CVD technique can provide a relatively thin application which impairs the properties of the liner material to a smaller extent and provides economies in the use of the coating material.

The polyparaxylylene coating is a coating which increases slip capability, is solvent-resistant, and chemically inert, and is used in a very wide variety of applications, inter alia on electronic components and in medical technology. Polyparaxylylenes are polymers of a divalent xylene unit having the structure $-CH_2-(C_6H_{5-n})R_n-CH_2-$ where n=1 to 3, and with various possible substituents R, inter alia chlorine, fluorine, and amine. Said polymers are currently deposited in a standard CVD process from the pyrolyzed dimers on a very wide variety of surfaces, and inter alia on orthopedic cushions, for example liners.

There are also other known coatings intended for liners and having slip capability, made of polytetrafluoroethylene and of other dry-slip films.

It has now been found that although liners made of silicone can be coated with dry-slip films with the aid of CVD processes, the coating of other plastics cushion materials is however difficult, particularly when these are fluid-filled materials. Coating of filled elastomers, of elastomer gels, in particular polyurethane gels, or of plasticized thermoplastics (flexible plastics, for example flexible PVC), and also of hydrophilic polyurethane generally, is not possible with known CVD- or PVD-coating processes, or cannot be achieved with the desired quality.

In particular, it has not hitherto been possible to coat flexible polyurethanes and polyurethane gels with thin layers of dry-slip films. Polyurethane liners, in particular polyurethane gel liners and flexible polyurethane liners, are therefore frequently merely treated with sprays and with liquid or soft lubricants. A coating method using TPU (thermoplastic polyurethane) derived from solution does not give satisfactory quality. When polyurethane liners are coated with non-polyurethane-based, unpolar and, respectively, non-hydrophilic polymers, the results are non-uniform deposition, variations in layer thicknesses, heterogeneity, cracking, and large areas of non-adhesion. The liners thus coated are useless, and even if they could actually be used they exhibit premature wear, or a high level of wear.

The same also applies to coatings intended for application on other orthopedic cushions.

SUMMARY

The invention is based on the object of providing an orthopedic cushion made of a fluid-filled elastomer, of an elastomer gel, of a plasticized thermoplastic, or of a polyurethane, with a coating which reduces friction and increases the slip capability of the surfaces on themselves and on the skin of a user, and which can be applied uniformly with secure adhesion, does not impair the functional properties of the cushion material, and is durable when the cushion is exposed to severe mechanical load, in particular when the cushion is subjected to extension.

Said object is achieved via a process in which the fully polymerized polyurethane cushion is subjected to at least one pretreatment step in which volatile constituents are extracted from the surface, and the cushion is subsequently immediately coated with a nonpolar polymer coating which increases slip capability (of the cushion surfaces on one another, or in relation to orthopedic components or textiles, or themselves), in particular a polymeric dry slip film.

Surprisingly, it has been found possible, in the pretreatment step specifically implemented prior to the coating process, to extract, from the surface, water and other volatile constituents, for example monomer residues or processing aids and solvents, and the additives and auxiliaries present in the material, whereupon a uniformly adherent coating can be applied, without extracting, across the entire volume of the cushion material, any excessive amount of the extenders (fluid fillers) and/or plasticizers that are present therein and that are essential for mechanical serviceability.

The pretreatment appears firstly to produce a non-equilibrium distribution which permits good-quality coating of the surface.

If the cushion material is composed of plasticizer-free polyurethane, the pretreatment primarily serves to remove, from the hydrophilic polyurethane, water absorbed from the environment, since water content otherwise inhibits uniform coating.

The invention can be applied to a very wide variety of filled or plasticized materials, or generally to polyurethanes.

In the event that polyurethane is used for the cushion of the invention, this particularly preferably involves a flexible polyurethane or a polyurethane gel. The term "flexible" is used here for polyurethanes with Shore 00 hardness from 15 to 50, preferably from 20 to 30; these require no plasticizer. Flexible polyurethanes and polyurethane gels are particularly suitable for orthopedic purposes, and are generally hydrophilic.

Gels are generally systems made of a macromolecular or colloid network (finely dispersed and structure-forming solid phase), filled with a fluid medium that can move relatively freely (expander phase). If the expander phase is water, the term hydrogel is used. The term polyurethane gels encompasses polyurethane hydrogels and preferably here polyurethane-only gels, in which not only the high-molecular-weight structural phase but also the fluid expander phase is composed of polyurethane components. In one particular possibility here, there is a loosely crosslinked or else under-crosslinked polyurethane structure filled with an excess of isocyanate-reactive component (generally polyol).

It is possible to use other elastomer gels or filled elastomers for the cushion of the invention. Elastomers are "filled" elastomers when there is a substance present that is liquid at room temperature or body temperature and which has not been covalently chemically bound into the crosslinking system of the elastomer. If the degree of crosslinking is relatively low and the degree of filling is high, the filler can also be regarded as gel dispersion medium, and the entirety of the filled elastomer can also be regarded as an elastomer gel. If the filler is water, the associated gels are termed "hydrogels". Oil fillers used in particular are silicone oils or hydrocarbon oils, e.g. medicinal white oils.

Examples of filled elastomers are in particular oil-filled rubber polymers and particularly oil-filled rubber copolymers. The rubbers encompass natural rubber and synthetic rubbers.

Thermoplastic and other elastomers which are suitable for the cushion materials are in particular copolymers using α-olefins and/or styrene, in particular styrene-butadiene-styrene block copolymers (SBS), styrene-ethylene-butylene-styrene block copolymer (SEBS), styrene-isoprene-styrene copolymer (SIS), styrene-ethylene-propylene copolymer (SEP), styrene-ethylene-ethylene-propylene-styrene copolymer (SEEPS), styrene-ethylene-propylene-styrene copolymer (SEPS), and styrene-ethylene-butylene copolymer (SEB).

Other suitable cushion materials are plasticized thermoplastics, in particular plasticized PVC. These comprise plasticizers in order to render the polyvinyl chlorides, which are otherwise brittle and rigid, suitable for cushions.

It is preferable to carry out at least one vacuum treatment and/or drying treatment. Vacuum treatment and drying are carried out as alternatives or in combination, and preferably respectively individually or together for a period that is to be determined experimentally in preliminary experiments. Polyurethane cushions can be treated to constant weight. It is possible to carry out other pretreatment steps prior to, after, or optionally (if undertaken separately) between the vacuum treatment step and the drying step. "Immediately subsequently" means that no insertion of prolonged times for storage or for transport is permitted between pretreatment and coating step, i.e. that no interruption of the process is permitted between pretreatment and coating, since otherwise the material can subsequently supply volatile substances from the interior of the cushion to the surface, thus becoming brittle, or, in the case of polyurethane, could absorb more water. It is currently assumed that no more than 12 hours are permitted to expire between pretreatment and coating, unless the pretreated cushion is protected via particular measures during storage. Storage in vacuo or in a drying chamber, or conditioning of the cushion at an elevated temperature under selected conditions, e.g. in a particular atmosphere, are considered where appropriate to be part of the pretreatment process and are sometimes possible, e.g. in the case of polyurethane.

The extraction of water and of other volatile constituents can be achieved by using solely a drying process, which should be carried out under the mildest possible conditions, i.e. at a moderate temperature. The maximum temperature that can be used depends on the data for the cushion material used. It is preferable to operate at a temperature from room temperature to 80° C. In one preferred embodiment, the cushion is treated in an oven at a temperature of from 30 to 60° C., for example at about 40° C. Polyurethane cushions can be dried to constant weight overnight. However, the drying process can also be combined with other measures for the extraction of volatile constituents, in particular with a vacuum treatment.

As an alternative to the drying process at an elevated temperature in an oven, the extraction of water and of other volatile constituents can also be achieved by a treatment in vacuo, preferably over a period of from half an hour to a plurality of hours, more preferably over from 2 to 8 hours, in particular over from 4 to 6 hours, or to constant weight. A suitable method is a treatment at a residual pressure of about 0.1 to 100 mbar, preferably from 5 to 15 mbar.

In an alternative embodiment, the treatment can take place in a vacuum oven with simultaneously elevated temperature (for example from 25 to 40° C.).

In one particularly preferred embodiment, the coating process uses a chemical or physical gas-phase deposition process. These processes are known in the prior art and therefore require no further description. The expression "chemical gas-phase deposition (CVD)" is used when the material for the coating forms during the vapor deposition process within the gas space and/or on the surface to be coated, from process gases which include the starting materials. The expression "physical gas-phase deposition (PVD)" is used when a coating material is merely vaporized and in turn deposited, without any chemical alteration. Suitable apparatuses for the conduct of said processes are known by way of example from U.S. Pat. No. 3,246,627, U.S. Pat. No. 3,301,707, or U.S. Pat. No. 3,600,216.

To the extent that the desired coating material is also to be used to achieve a uniform thin coating from solution or via spray-application, these and other suitable coating processes can equally be used within the process of the invention, i.e. after the pretreatment that is described in more detail hereinafter.

A "thin" coating can be regarded as a coating of which the layer thickness is up to 10 µm, preferably up to 5 µm, and more preferably only up to 2.5 µm. Another essential factor for the quality of the coating is that the layer thickness is uniform.

To the extent that, as is preferred, the coating process uses a CVD process or PVD process, the pretreatment step for the extraction of water and of other volatile constituents can take place prior to the coating process in the coating chamber of the CVD apparatus or PVD apparatus itself, with or without temperature increase. To this end, a vacuum (without introduction of process gas) is applied for a particular time prior to the introduction of the gas mixture for the coating process.

However, it is preferable that the cushion to be coated is exposed prior to the coating process in the treatment chamber of the coating apparatus in a separate vacuum chamber installed upstream for about half an hour to six hours to the vacuum also provided for the coating process. The cushion is then transferred to the CVD chamber and coated.

Prior to the coating process, plasma treatment or corona treatment can take place as additional or alternative pretreatment step on the surface to be coated. This is particularly advantageously possible in the coating chamber of a CVD apparatus or PVD apparatus, these frequently being equipped in advance for said pretreatment.

In a particularly preferred embodiment, a poly(para-xylylene) can be used as coating agent, in particular an unsubstituted or halogen-substituted polyparaxylylene. The agent can be purchased with trademark Parylene® (Parea Tech Coating Inc, USA). As an alternative, it is possible to use other polymer coatings which increase the slip capability of the cushion material, in particular what are known as dry-slip films. Among the dry-slip films are also tetrafluoroethylene and various derivatives thereof.

It can also be advantageous that the cushion is subjected to at least one additional cleaning step within the pretreatment process. This preferably takes place prior to the drying process and/or vacuum treatment of the material, but can also be an intermediate or downstream step. The cleaning step can be composed of washing with water or water and soap, or of washing or rinsing with another agent, e.g. an organic solvent, and preferably in that case an alcohol. The cleaning step can also encompass a saturation or swelling process. By way of example, it is preferable to begin by washing the fully polymerized cushion with water and soap, or only with water, or with isopropanol, or with ethanol. It is possible to combine a plurality of cleaning steps, where these follow one another directly, or can be inserted at various points within the pretreatment process.

In one possible embodiment of the invention, washing and drying are first carried out, and are followed by rinsing with organic solvent, and then by a further drying step and/or vacuum treatment step.

One embodiment of the invention also provides that, prior to the coating process, an adhesion promoter is applied. Known silane-based adhesion promoters are suitable, examples being those used in the rubber industry. However, the use of an adhesion promoter is not regarded in principle as necessary, and in particular it is regarded as unnecessary when plasma treatment or corona treatment of the surface is undertaken prior to the coating process.

The invention therefore provides for the first time an orthopedic cushion made of a filled elastomer, of an elastomer gel, of a plasticized thermoplastic, or of a polyurethane, with a thin friction-reducing nonpolar and non-hydrophilic polymer coating in a uniform, thin layer. It was not possible hitherto to produce cushions coated in this way, in particular liners or shafts.

In principle, the process of the invention can be used to coat any soft and filled materials. However, the orthopedic cushion of the invention preferably involves a liner, an entire shaft, or a separate shaft cushion. Among the preferred cushions for which the invention is used are also orthotic cushions, where the intention is to use this method to render these dust-repellant and dirt-repellant. It is moreover possible to coat cushioning bandages of any type, e.g. foot bandages, knee bandages, or elbow bandages.

The location of the polymer coating can preferably be not only on the external side of the cushion but also on the internal side of the cushion which, in usage position, faces toward the skin. Despite the friction-reducing internal coating, there is no slip, even of a polyurethane gel cushion, because the cushion has very high conformability to the body of the user. The cushion of this invention can also have, in addition to the exterior cushion coating which by way of example provides better slip capability of the external area of a liner on itself and thus facilitates the application and removal of the liner, an inner coating which counteracts the fully non-slip performance of many cushion materials and thus likewise contributes significantly to the comfort of the wearer.

In a particularly preferred embodiment, the polymer coating is composed of a poly(para-xylylene), as stated above.

For the purposes of the invention, it is also particularly preferable that the coating is applied specifically in a layer thickness such that it does not split on extension of the liner by 30% in at least one spatial direction, and preferably does not split on extension by 50%. It has been found that as the application thickness of the coating reduces the coating becomes more elastic and resistant to splitting. However, a greater layer thickness contributes to longer practical service time of the liner, since it compensates inevitable abrasion. Layer thicknesses of from 50 to 500 nm or from 50 to 1000 nm are therefore regarded as ideal, where these can withstand extension of the liner of up to 100% in at least one longitudinal direction without splitting, or, if somewhat longer service time is desired, layer thicknesses above 500 nm to 2.5 µm, where these can withstand extension values up to at least 40%.

The ideal layer thickness is therefore highly dependant on the cushion material and on the shape, nature and usage position of the cushion, and has to be selected and tested by the person skilled in the art in accordance with requirements.

In an advantageous embodiment, there can be an adhesion promoter located between cushion material and polymer coating, as described above. Suitable adhesion promoters are known to the person skilled in the art, and in particular it is possible to use familiar silane adhesion promoters. The cushion material is as previously stated above in relation to the process.

Finally, the invention encompasses in general terms the use of poly(para-xylylene)s for coating an orthopedic cushion, in particular of a liner or of a shaft, made of a flexible polyurethane, of a polyurethane gel, or generally of a filled elastomer gel, of a filled elastomer (e.g. a filled rubber elastomer), or of a plasticized thermoplastic, such as plasticized PVC.

DETAILED DESCRIPTION

Some examples of possible embodiments of the invention are given below:

Liners were manufactured from polyurethane gels. The polyurethane gels used here were produced from:

A: glycerol-started polyether polyol based on propylene oxide having from 10 to 20% of terminal ethylene oxide and having average molecular weights of about 5000 to 6000, and B: modified HDI having from 10 to 20% NCO content; in an A:B ratio of from 100:5 to 100:30.

The additives used comprised only inert inorganic fillers and PU catalyst.

I. PRETREATMENT EXAMPLES

Process Example 1

The PU liner surface is first cleaned with water and soap, and then dried to constant weight overnight in an oven at 40° C. A coating process is then carried out.

Process Example 2

The PU liner surface is cleaned with isopropanol, then devolatilized to constant weight over a period of from to 6 hours at a residual pressure of from 10 to 20 mbar. A coating process is then carried out.

Process Example 3

The PU liner surface is pretreated as described in 2. Immediately prior to the coating process, the surface is pretreated in situ by igniting a plasma in vacuo in the same treatment chamber.

Process Example 4

The PU liner surface is
saturated with isopropanol for from 5 to 10 min;
rinsed with distilled water for from 5 to 10 min;
treated for 30 min in a mixture made of 100 parts of isopropanol and 1 part of silane A 174 (GE Silicones);
dried;
rinsed with isopropanol for 5 min;
kept at 115° C. for 30 min;
further pretreated as in process example 1 or 2.
A coating process is then carried out.

II. COATING EXAMPLE

For CVD coating with poly(para-xylylene)—unmodified—cyclic diparaxylylene was vaporized in vacuo at a temperature of about 150° C. and then pyrolyzed in a pyrolysis chamber at temperatures up to 650° C., in order to produce free paraxylyl monomers in the gaseous state. The monomer-containing process gas thus produced is introduced into a vacuum chamber which comprises the liner to be coated. The liner is held in the process vacuum chamber in such a way that the surfaces to be coated are exposed, i.e. are brought into contact with the monomer-containing gas. The process vacuum chamber with the liner can be maintained at approximately room temperature, i.e. temperatures from 20 to 30° C. The polymer, or the monomer polymerizing in situ, is deposited onto the exposed liner surfaces. The thickness of the resultant coating film can be adjusted inter alia by way of the duration of the coating procedure.

An inventive example is compared below with a comparative example in terms of service properties.

Comparative Example

A fully polymerized PU liner of the specification given above was washed with water and soap and then with isopropanol, in order to free it from release agent, fat, and adherent dirt, and was then subjected to the coating process described in B. Table 1 gives the results.

Inventive Example

A fully polymerized PU liner of the specification given above was pretreated as in an experimental example and was then subjected to the coating process described in B. Table 1 collates the results. All of the liners in experimental examples 1 to 4 complied with the specifications in the right-hand column of the table.

TABLE 1

| Property | Comparative example | Inventive example |
| --- | --- | --- |
| Appearance | heterogeneous, nonuniform, color-shimmer effect (due to different thicknesses of layer deposition in different regions, resulting in optical interference phenomena) | uniformly milky, homogeneous appearance with no color variation |
| Splitting behavior | coating splits rapidly because of the very great differences in amounts of layer deposited at sites with very thin layer and sites with very thick layer | uniform layer leads to uniform splitting only at relatively high extension |
| Extension performance | surface becomes uneven on extension | appearance unaltered on extension and on removal of load |
| Slip properties | marked stick-slip effect when the layers slide over one another | smooth coating with slip capability, resulting in no stick-slip effect when the layers slide over one another |
| Friction reduction (to ASTM 1894) stated as dimensionless coefficient (Force to move the sample horizontally)/(Downward force of sled); smaller coefficient means less friction | static: from 1.5 to 2.6  kinetic: from 1.9 to 2.9 | static: from 0.3 to 0.6  kinetic: from 0.2 to 0.5 |

What is claimed is:

1. A process for producing an orthopedic cushion which has a friction-reducing coating, comprising:
    subjecting an orthopedic cushion material which is made of a filled elastomer, an elastomer gel, a plasticized thermoplastic, or a polyurethane to at least one pretreatment step in the form of a vacuum treatment or a drying process in which volatile constituents present in the cushion material are extracted out of a surface of the cushion material without extracting across an entire volume of the cushion material an amount of additives and auxiliaries that are needed for mechanical serviceability of the cushion, wherein the volatile constituents include at least one selected from the group consisting of additives, solvents, auxiliaries, processing aids, monomers and water;

subsequently coating the cushion with a nonpolar polymer coating which increases slip capability, wherein the coating is applied using a chemical vapor-phase deposition (CVD) or physical vapor-phase deposition (PVD) process.

2. The process of claim 1, wherein the extraction of the volatile constituents is performed using a drying process is carried out at a temperature of from 30° C. to 60° C.

3. The process of claim 1, wherein the extraction of the volatile constituents is performed using vacuum treatment carried out with a residual pressure from 0.1 to 100 mbar.

4. The process of claim 1, wherein, prior to the coating process, a plasma treatment or a corona treatment is applied to the cushion surface to be coated.

5. The process of claim 1, wherein, prior to the coating process, an adhesion promoter is applied.

6. The process of claim 1, wherein the plasticized thermoplastic comprises an elastomeric copolymer that includes at least one of the group comprising: styrene-butadiene-styrene block copolymer (SBS), styrene-ethylene-butylene-styrene block copolymer (SEBS), styrene-isoprene-styrene copolymer (SIS), styrene-ethylene-propylene copolymer (SEP), styrene-ethylene-ethylene-propylene-styrene copolymer (SEEPS), styrene-ethylene-propylene-styrene copolymer (SEPS), and styrene-ethylene-butylene copolymer (SEB).

7. The process of claim 6, wherein poly(para-xylylene) is used for a polymeric dry slip film.

8. A process for producing an orthopedic cushion which has a friction-reducing coating, comprising:

subjecting an orthopedic cushion material which is made of a polyurethane to at least one treatment step in the form of a vacuum treatment or a drying process in which volatile constituents present in the cushion material are extracted out of a surface of the cushion material without extracting across an entire volume of the cushion material an amount of the additives and auxiliaries that are needed for mechanical serviceability of the cushion, wherein the volatile constituents include at least one selected from the group consisting of additives, solvents, auxiliaries, processing aids, monomers and water, and wherein the at least one treatment step produces a non-equilibrium distribution of the volatile constituents across the surface and water absorbed from the environment is removed from the polyurethane;

subsequently coating the cushion with a nonpolar polymer coating which increases slip capability, wherein the coating is applied using a chemical vapor-phase deposition (CVD) or physical vapor-phase deposition (PVD) process.

9. The process of claim 8, wherein the polymer coating increasing slip capability is a polymeric dry slip film.

10. A process for producing an orthopedic cushion, comprising:

forming the orthopedic cushion of at least one of a filled elastomer, an elastomer gel, a plasticized thermoplastic, or a polyurethane;

extracting volatile constituents, which include at least one from the group consisting of additives, solvents, auxiliaries, processing aids, monomers and water, out of a surface of the orthopedic cushion via a vacuum treatment or a drying process without extracting, across an entire volume of the cushion material, an amount of the additives and auxiliaries that are needed for mechanical serviceability of the cushion;

subsequently coating the surface with a nonpolar polymer coating which increases slip capability for the orthopedic cushion, the coating is applied using a chemical vapor-phase deposition (CVD) or physical vapor-phase deposition (PVD) process.

11. The process of claim 10, wherein the coating provides a polymeric dry slip film.

12. The process of claim 10, wherein the extraction of volatile constituents is carried out using the drying process at a temperature of from 30° C. to 60° C.

13. The process of claim 10, wherein the extraction of volatile constituents is carried out using the vacuum treatment with a residual pressure from 0.1 to 100 mbar.

14. The process of claim 10, further comprising, prior to coating the surface, applying a plasma treatment or a corona treatment on the surface to be coated.

15. The process of claim 10, wherein the nonpolar polymer coating includes poly(para-xylylene).

16. The process of claim 10, further comprising applying an adhesion promoter prior to coating the surface.

* * * * *